United States Patent [19]

Kao et al.

[11] Patent Number: 5,504,116
[45] Date of Patent: Apr. 2, 1996

[54] LIDOCAINE FOR THE MANAGEMENT OF PRETERM LABOR

[75] Inventors: Chien-Yuan Kao, Pound Ridge; Shuya Wang, Brooklyn, both of N.Y.

[73] Assignee: Research Foundation of State University of New York, Albany, N.Y.

[21] Appl. No.: 249,875

[22] Filed: May 26, 1994

[51] Int. Cl.$^6$ .................................................. A61K 31/16
[52] U.S. Cl. ......................... 514/626; 514/821; 514/935
[58] Field of Search .................................. 514/626, 821, 514/935

[56] References Cited

U.S. PATENT DOCUMENTS

| | | | |
|---|---|---|---|
| 5,091,387 | 2/1992 | Evans et al. | 514/278 |
| 5,095,003 | 3/1992 | Goetz et al. | 514/9 |
| 5,175,159 | 12/1992 | Bock et al. | 514/221 |
| 5,198,463 | 3/1993 | Pettibone et al. | 514/450 |
| 5,204,349 | 4/1993 | Bock et al. | 514/253 |
| 5,225,528 | 6/1993 | Bock et al. | 530/321 |
| 5,242,947 | 7/1993 | Cherskey et al. | 514/628 |

OTHER PUBLICATIONS

Inoue Y., Sperelakis N. Gestational change in $Na^+$ and $Ca^{2+}$ channel current densities in rat myometrial smooth muscle cells. Am. J. Physiol. 1991; 260:C658–C663.

Miyoshi H., Urabe T. Fujiwara A. Electrophysiological properties of membrane currents in single myometrial cells isolated from pregnant rats. Eur J. Physiol. 1991; 419:386–393.

Inoue, Y., Nakao K., Okabe, K., Izumi H., Kanda S., Kitamura K., Kuriyama H. Some electrical properties of human pregnant myometrium. Am. J. Obstet. Gynecol. 1990; 162:1090–1098.

Yoshino M., Wang S. Y., Kao C. Y. Ionic currents in smooth myocytes of the pregnant rat uterus. J. Gen. Physiol. 1989; 94:38a (abstract).

Ohya Y., Sperelakis N. Fast $Na^+$ and slow $Ca^{2+}$ channels in single uterine muscle cells from pregnant rats. Am. J. Physiol. 1989; 257:C408–C412.

Young R. C., Herndon–Smith L. Characterization of sodium channels in cultured human uterine smooth muscle cells. Am. J. Obstet. Gynecol. 1991; 164:175–181.

Nakai Y., Kao C. Y. Changing properties of $Na^+$ and $Ca^{2+}$ components of the early inward current in rat myometrium during pregnancy. Fed. Proc. 1983; 42:313 (abstract).

Kao C. Y., McCullough, J. R. Ionic currents in the uterine smooth muscle. J. Physiology (London) 1975; 246:1–36.

Kao C. Y. Wakui, M., Wang, S. Y., Yoshino, M. The outward current of the isolated rat myometrium., J. Physiol. 1989; 418:20P.

Chemical Abstracts 113:52387, 1989, Li et al.
Chemical Abstracts 90:162013, 1979, Willdeck–Lund et al.
Chemical Abstracts 90:197480, 1978, Lampa et al.
"Facts and Comparisons", Olin et al. (Editors), J. B. Lippincott Co., St. Louis, MO, 1990, pp. 145–145a.

Primary Examiner—Marianne M. Cintins
Assistant Examiner—M. Moezie
Attorney, Agent, or Firm—Morgan & Finnegan

[57] ABSTRACT

The use of lidocaine or other Class I cardiac antiarrhythmic compound in the management of preterm labor and the stoppage of labor preparatory to cesarian delivery, is disclosed. The electrophysiological effects of lidocaine on the sodium, calcium and potassium channels of freshly dissociated myocytes from late-pregnant rat uteri with the tight-seal patch-clamp method are presented. Dose-response relations on the sodium and calcium currents, and effects on the availability relation for sodium current are also presented. Also disclosed are the effects of chronic administration of lidocaine on the duration of pregnancy.

6 Claims, 5 Drawing Sheets

FIG. 3A
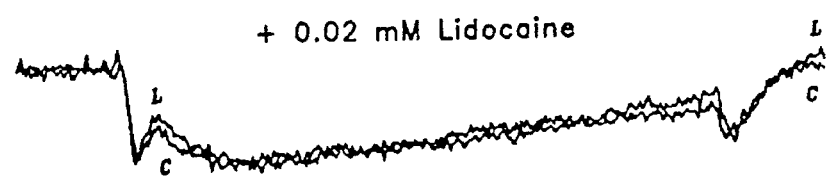
FIG. 3B
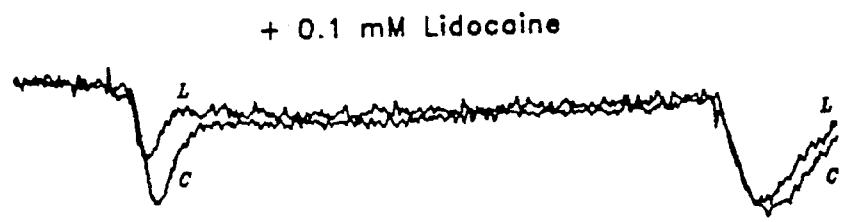
FIG. 3C
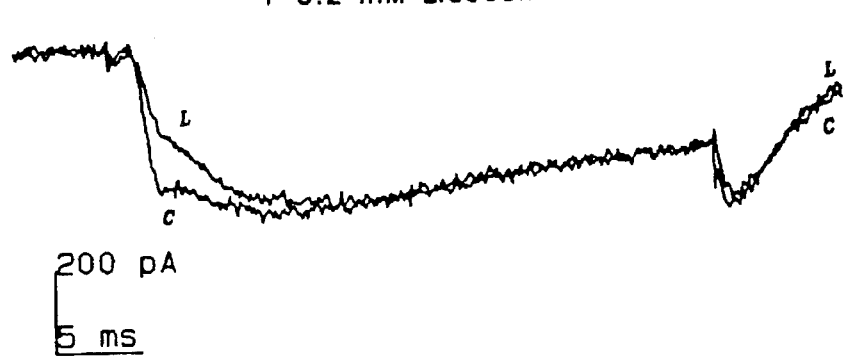

LIDOCAINE FOR THE MANAGEMENT OF PRETERM LABOR

This invention was made with government support under Grant Number HD 00378 awarded by The National Institute of Child Health and Development. The government has certain rights in the invention.

TECHNICAL FIELD

The invention relates to methods of using sodium channel affecters, such as lidocaine and other Class I cardiac anti-arrhythmic agents, to manage preterm labor and stop labor preparatory to cesarean delivery.

BACKGROUND ART

Preterm labor and its complications are major perinatal public health issues in developed societies today. They account for half of all infant deaths and three-quarters of long-term morbidity. They impose a heavy burden on the national economy, because of the high costs of special care in both the neonatal period and over the life-span of survivors. Many survivors also have diminished quality of life because of physical damage resulting directly from prematurity.

The rationale of all current empirical methods of managing preterm labor is to attempt tocolysis with the aim of reducing the frequency and force of uterine contractions and delaying birth. Drug therapy for such tocolysis includes $Mg^+$-infusion, inhibitors of prostaglandin synthesis (e.g., indomethacin), β-adrenergic agonists (e.g., ritodrine, tertbutaline), and calcium-channel blocking agents (e.g., nifedipine). Although each of these alternatives can temporarily reduce premature contractions, none of them has proven to be effective in substantially delaying parturition. The pharmacodynamic mechanisms or these therapies in relation to the management of preterm labor are discussed briefly below:

In visceral smooth muscles, activation of β-adrenergic receptors often leads to hyperpolarization and relaxation. Underlying this phenomenon is a $G_s$ protein-mediated and protein kinase A-catalyzed increase in the openings of a class of large-conductance $Ca^{2+}$-activated $K^+$ channel[20]. In the late-pregnant uterine myocyte, however, the functional expression of this class of $K^+$ channels is depressed[8]. So, it is unclear how effective an agent which works via such $K^+$ channels would be in modulating excitability of the myometrium. Moreover, β-adrenergic agonists also stimulate the synthesis of prostaglandins[21]. Perhaps because of these reasons, ritodrine is effective for only a few days, and does not affect the pregnancy outcome[5]. Moreover, it can produce cardiovascular side-effects in some recipients.[5]

The use of calcium-channel blocking agents for uterine tocolysis is now being tested, but it is too early for statistically evaluable results. However, from physiological and pharmacological considerations, such agents are less than ideal. The primary concern militating against their use is that there are no significant demonstrated differences between the L-type calcium channels in the myometrium[7] and those in many other types of smooth muscles, including various vascular smooth muscles. Unless an agent can selectively block the myometrial calcium channels, it will produce side-effects on a wide range of other tissues. For similar reasons of a lack of specificity, inhibitors of prostaglandin synthesis, although capable of inducing myometrial tocolysis, are liable to produce side-effects[6].

Under physiological conditions, contractions in muscular tissues is the end result of a sequence of processes which begins with the generation of electrical signals in the cellular surface membrane, influx or release from stores of calcium ions, activation and cross-bridge formation between actin and myosin filaments. In most mammalian visceral smooth muscles, the electrical signals, the action potentials, are based on voltage-gated calcium channels.

Unique among them, small tissue-level multicellular strips of uterine smooth muscle have been shown to produce both sodium and calcium currents. C.Y. Kao et al., Ionic currents in the uterine smooth muscle, J. Physiology (London) 246: 1–36, 1975. In freshly dissociated single myocytes from the uterine muscle, both voltage-gated sodium channels and voltage-gated calcium channels have been demonstrated. The functional expression of the myometrial sodium channel is under the control of estrogen. The coexistence of the two different types of channels has been demonstrated in the uterine myocytes of rats (freshly dissociated cells[7,10,11]), rabbits (freshly dissociated, unpublished observations of S. Y. Wang and C. Y. Kao), and women (freshly dissociated, unpublished observations of S. Y. Wang, C. Y. Kao and D. Nanda; tissue-cultured[12]). Significantly, in the rat uterine myocytes, the ratio of the peak sodium/calcium currents changes during the course of pregnancy, such that the contribution of the sodium channel in generating action potentials progressively increases towards term[7,13]. In the pregnant rat, the sodium channels appear to be pivotal in the generation of fast repetitive action potentials to enable excitation of the entire uterus[7].

U.S. Pat. Nos. 5,091,387; 5,095,003; 5,198,463; 5,175,159; 5,204,349 and 5,225,528 describe oxytocin antagonists as useful in the treatment of preterm labor. (Oxytocin is a hormone which stimulates the frequency and force of uterine muscle contractions). U.S. Pat. No. 5,242,947 describes polyamines and their use as ionic-channel regulating agents, but does not describe their use in the treatment of pre-term labor. None of these U.S. patents discusses lidocaine or its use to treat pre-term labor.

Inoue and Sperelakis (1991), Am. J. Physiol. 260: C658–C663, studied the changes in ionic channel densities over much of gestation, using the patch clamp method in freshly isolated smooth muscle cells of myometrium. They conclude that the fraction of cells which possess fast sodium channels increases during gestation and state that

[t]hese results suggest that the role of fast $Na^+$ channels in myometrial activity becomes more and more important as term approaches.... [T]he fast $Na^+$ current may be involved in spread of excitation.

See abstract and p. C661, col. 2. They further note that "[t]he role of the fast $Na^+$channel is not known" (p. C661, col. 2) and suggest that their increased number may result in faster propagation of excitation, and hence, more forceful contraction during parturition (p. C662, col. 1), but state that "[f]urther experiments are necessary to clarify the physiological role of the fast $Na^+$ channels in pregnant myometrial smooth muscle cells." (P. C662, col. 2).

Miyoshi et al. (1991), Eur J. Physiol. 419:386–393, applied the whole-cell voltage-clamp method to single smooth muscle cells prepared from pregnant rat myometrium (17–20 days of gestation). In a small number of preparations (in 2 out of 30 preparations) a tetrodotoxin ("TTX")-sensitive fast inward current was detected, suggesting that the channel for this current is equivalent to the $Na^+$ channel in nerve cells. See abstract and p. 322, col. 1. These authors conclude that "[t]his observation clearly indicates that the contribution of $Na^+$ channels to the action potential in the physiological condition is extremely small, if any." See p. 332, col. 1.

Inoue et al. (1990), Am. J. Obstet. Gynecol. 162:1090–1098, studied the membrane properties of human pregnant myometrium with the conventional microelectrode and patch clamp methods. They state that their "results confirmed the importance of calcium and sodium ions for generation of action potential in human myometrium," even though they failed to record a sodium current. See p. 1097, col. 1.

Kao et al. (1989), J. Physiol. 418:20P, studied myocytes from 17–21 day pregnant rats with the whole-cell tight seal patch-clamp method. They reported recording sodium and calcium inward currents as well as outward currents.

Ohya and Sperelakis (1989), Am. J. Physiol. 257:C408-C412[11] reported that TTX-sensitive fast $Na^+$ channels existed in pregnant rat myometrium (day 18) by using the whole cell voltage-clamp method, but did not investigate the changes in this channel during gestation. They conclude that "the major ion channels in the cell membrane of pregnant rat uterus . . . are TTX-sensitive fast $Na^+$ channels and dihydropyridine-sensitive slow $Ca^{2+}$ channels". See abstract. They state that "the role of fast $Na^+$ channels is unknown" but that "insertion of fast $Na^+$ channels into the cell membrane during pregnancy, would allow for . . . faster propagation over the entire uterus . . ., as required for parturition." They conclude that "further study is required to clarify the role played, if any, of the fast $Na^+$ current is uterine physiology." See p. C411, Col. 2.

Young and Herndon-Smith (1991), Am. J. Obstet. Gynecol. 164:175–181[12], conducted voltage-clamp studies using the whole-cell patch clamp technique on single cells of cultured human uterine smooth muscle obtained from term pregnancies. A TTX-sensitive fast sodium channel was observed in the cultured human myocytes. The authors state that "[t]he physiologic role of the sodium channel is not immediately apparent" (p. 179, col. 2) and further state that sodium channels "will not likely contribute to the rise of the action potential" (p. 180, col. 2).

Nakai and Kao (1983), Fed Proc 42:313[13], reported in abstract form, using a multicellular preparation of pregnant rat myometrium, that the ratio of sodium current to calcium current increases as term approaches. They suggested "such a change could account for the faster rate of rise of the action potentials at term than in mid-pregnancy."

The present invention relates to the use of lidocaine and other Class I antiarrhythmic drugs to manage preterm labor. In particular, lidocaine has advantages over the drugs of the prior art in that it is expected to control the prematurely excitable and contracting human uterus and is also expected to have few or limited side-effects on the heart, vasculature, and the fetus, since the uterine muscle sodium channels are sensitive to concentrations of lidocaine too low to affect cardiac sodium channels, or potassium or calcium channels.

While some of the above-cited references speculate that the role of sodium channels may increase in importance as term approaches, the role of the sodium channels is acknowledged to be unknown. None of the above-cited references describe or suggest the use of a sodium channel affecter, such as lidocaine, as a potential tocolytic agent.

DISCLOSURE OF THE INVENTION

The invention relates to methods of using a sodium ($Na^+$) channel affecter, such as lidocaine or other Class I cardiac antiarrhythmic agent, and pharmaceutically acceptable salts thereof, as a potential tocolytic agent (i.e., an agent that inhibits uterine contractions) to manage preterm labor and stop labor preparatory to cesarean delivery. These compounds are useful in animals, preferably mammals and especially humans.

Thus, one embodiment of the invention relates to a method for relaxing uterine smooth muscle or reducing uterine contractile activity by inhibiting voltage-gated sodium channel activity comprising administering to a patient a sodium channel inhibiting amount of a Class I cardiac antiarrhythmic compound. Another embodiment of the invention relates to a method for inhibiting premature labor comprising administering to a patient a therapeutic amount of a Class I cardiac antiarrhythmic compound. Preferably, the Class I cardiac antiarrhythmic compound is either tocainide or lidocaine, most preferably lidocaine.

BRIEF DESCRIPTION OF THE DRAWINGS

FIG. 3A, B and C. Effect of lidocaine on the $I_{Na}$ and $I_{Ca}$ of freshly dissociated late-pregnant rat uterine myocytes. Voltage-protocol shown on top; holding potential, −80 mV; 30 ms step to 10 mV, where inward currents are maximum.

Traces labelled C are controls, before lidocaine, and traces labelled L are taken 5 min after application of lidocaine. Myocytes are: (A) from 18-day pregnant uterus, 109 pF; (B) from 20-day pregnant uterus, 188 pF; and (C) from 19-day pregnant uterus, 190 pF. Records demonstrate variability of inward currents in different myocytes, but co-existence of $I_{Na}$ and $I_{Ca}$ in all cells. Superimposed traces show clearly the relatively selective actions of lidocaine on $I_{Na}$ with very little effect on $I_{Ca}$.

Figure 4B:
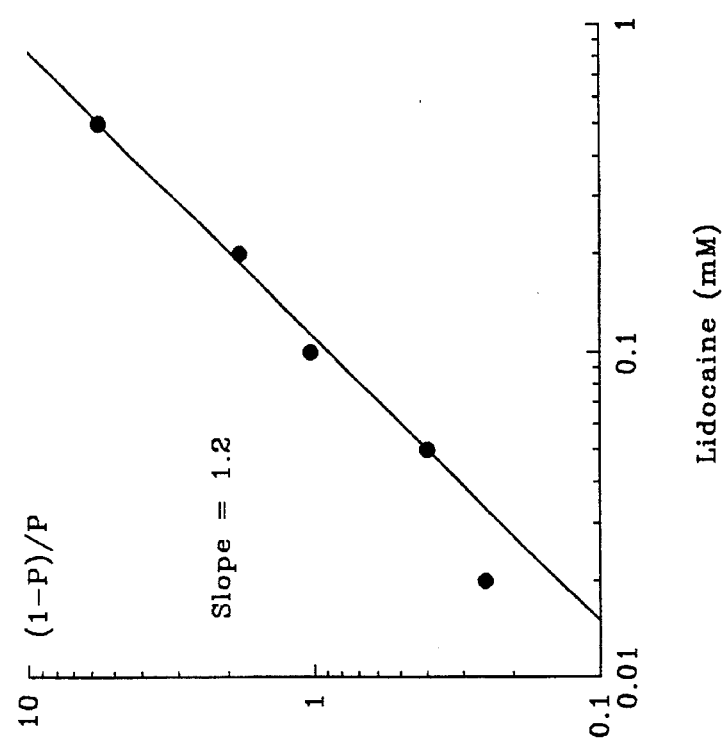
Figure 4A:
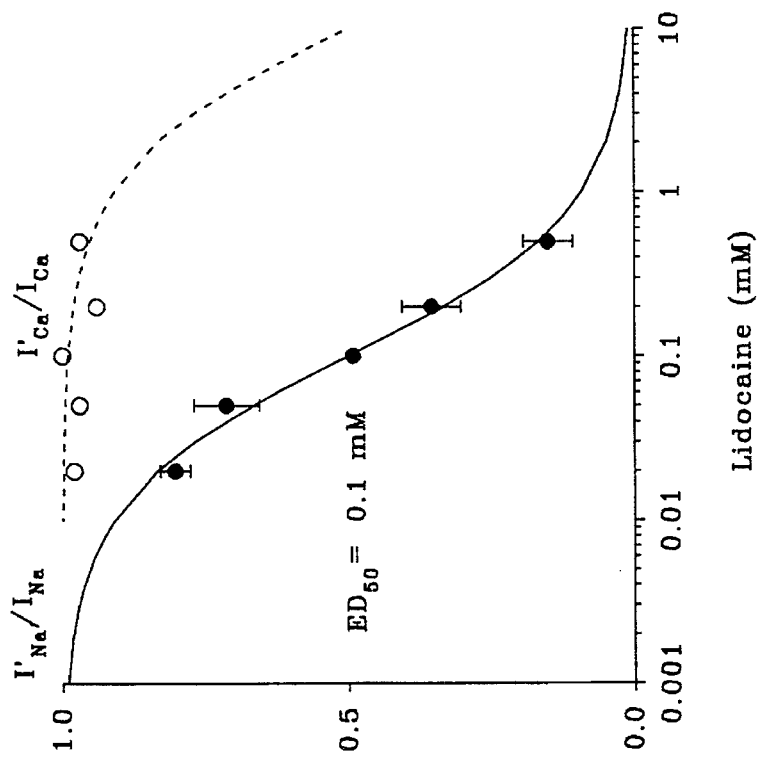

FIGS. 4A and B. Dose-response relations of lidocaine on $I_{Na}$ and $I_{Ca}$ of freshly dissociated uterine myocytes. (A) Semi-log plot in which the abscissa is concentration of lidocaine on a log scale, and the ordinate is residual current in lidocaine ($I'_{Na}$ or $I'_{Ca}$) normalized to the corresponding current before lidocaine ($I_{Na}$ or $I_{Ca}$). Filled symbols for $I'_{Na}/I_{Na}$, representing the means ± S. E. M. of 4–5 myocytes at each concentration of lidocaine. Solid line is drawn according to bimolecular reaction scheme: $y=1-(1+ED_{50}/[lidocaine])^{-1}$, where [] denotes concentration of lidocaine and $ED_{50}$ is the [lidocaine] at which $I'_{Na}/I_{Na}$ is 0.5. Hollow symbols for $I'_{Ca}/I_{Ca}$ in same myocytes used for $I'_{Na}/I_{Na}$ values. Broken line is possible dose-response relation based on the assumption of a similar bimolecular reaction with lidocaine. In such a case, the possible $ED_{50}$ would be about 10 mM. However, the relation could extend more to the right into higher concentrations of lidocaine, with correspondingly higher $ED_{50}$. (B) Hill plot of dose-response relation where log (1-P)/P is plotted against log [lidocaine]. $P=I'_{Na}/I_{Na}$. $ED_{50}$ is [lidocaine] at which (1-P)/P=1. The slope of the curve, 1.2, is consistent with a bimolecular reaction without cooperativity.

Figure 5:
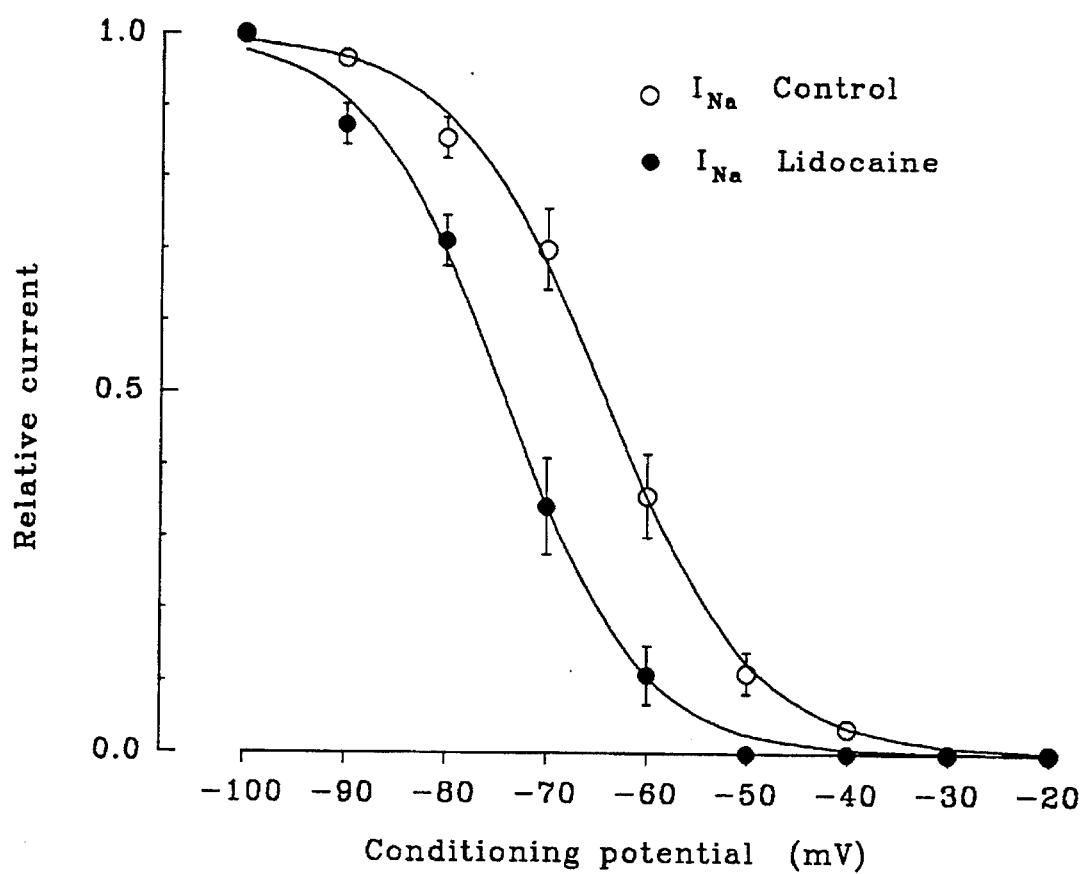

FIG. 5. Effect of lidocaine on the voltage-steady-state inactivation ("availability") relation of $I_{Na}$ in freshly dissociated uterine myocytes. Two-pulse method in which a conditioning pulse (100 ms) varied from −100 to −10 mV, followed immediately by a testing pulse (6 ms) to 10 mV at which $I_{Na}$ is maximum. The method determines the fraction of all $I_{Na}$ which can be elicited (hence, available) from different preexisting membrane voltages. 5 μM nisoldipine was added to bathing medium to block $I_{Ca}$ and isolate $I_{Na}$ for study. 8 myocytes were used for the control, pre-lidocaine state. The same myocyte was used after 5 min in 0.22 mM lidocaine (2× $ED_{50}$), but only in 5 was the complete sequence successful. Data points are means ±S. E. M.; hollow symbols for control and filled symbols for lidocaine-treated state. Abscissa is conditioning membrane voltage (V), and ordinate is $I_{Na}$ in the presence of a conditioning voltage step normalized to $I_{Na}$ in the absence of the conditioning step (relative current). Solid lines are drawn according to Boltzmann distributions: $y [1+exp (V-V_h)/k]^{-1}$ where V is conditioning membrane voltage, and $V_h$ when relative current=0.5 (i.e., half-inactivation voltage), k is the slope factor, which describes the voltage-sensitivity of the inactivation process. $V_h$ in the control state is −64 mV. In lidocaine, the entire curve is shifted towards more negative voltages, with $V_h$ at −74 mV. The slope factor, k, is 7.4 mV for the control state and 6.8 mV for the lidocaine-affected state. The small difference suggests that lidocaine did not alter the voltage-sensitivity of the inactivation process. Lidocaine reduces the available fraction of $Na^+$ channels to generate current for action potentials, and may thereby reduce myometrial excitability.

MODES FOR CARRYING OUT THE INVENTION

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

The invention comprises methods for using a sodium channel affecter, such as lidocaine or other Class I cardiac antiarrhythmic agent, and pharmaceutically acceptable salts thereof, to manage preterm labor and stop labor preparatory to cesarean delivery.

One embodiment of the invention relates to a method for relaxing uterine smooth muscle or reducing uterine contractile activity by inhibiting voltage-gated sodium channel activity comprising administering to a patient a sodium channel inhibiting amount of Class I cardiac antiarrhythmic compound. Another embodiment of the invention relates to a method for inhibiting premature labor comprising administering to a patient a therapeutic amount of a Class I cardiac antiarrhythmic compound. Preferably, the Class I cardiac antiarrhythmic compound is either tocainide or lidocaine, most preferably lidocaine.

Lidocaine is a common local anesthetic agent which is also used as a cardiac antiarrhythmic agent. The inventors have shown that lidocaine selectively blocks voltage-gated sodium channels and reduces membrane excitability in freshly dissociated pregnant-rat uterine myocytes. The inventors have also shown that intramuscular injections of lidocaine can prolong the duration of gestation in pregnant rats by 7%. Concentrations of lidocaine blocking sodium channels of uterine myocytes have no effects on myometrial $K^+$ or $Ca^{2+}$ channels, and are about ⅕ of those affecting sodium channels of cardiac ventricular myocytes, therefore, it is expected that the use of lidocaine to prolong gestation will have little or no side-effects on heart muscle.

The various lines of evidence presented in the examples herein show that lidocaine can reduce the excitability of the uterine muscle. The effects are exerted almost entirely on the voltage-gated sodium channels in the uterine myocytes, with very little effect on the coexisting voltage-gated calcium channels and potassium channels. From this perspective alone, one would expect that for the same degree of tocolysis produced by some calcium-channel blocking agent, lidocaine should produce less side-effects on other smooth muscle tissues and organs, none of which has been shown to contain any voltage-gated sodium channels (see comments in [7]).

The effects of lidocaine on the myometrium are essentially similar to those of some class 1 cardiac antiarrhythmic agents. Potential side-effects would be primarily on the heart. In assessing the usefulness of lidocaine for managing preterm labor, the actions of lidocaine on the myometrium and on the myocardium must be compared. Although comparing the effects on isolated myocytes is only the first step, two factors are particularly relevant. First, the density of $Na^+$ current is up to 5–7 μA/cm$^2$ of cell surface in the uterine myocyte[7,12], but is in the range of 1 mA/cm$^2$ in the cardiac myocyte[22]. Since the unitary conductances of single native sodium channels from various tissues are relatively uniform, the difference in current densities suggests that there are probably far fewer sodium channels in the uterine myocyte than in the cardiac myocyte. Even if the two types of myocytes have the same affinities for lidocaine, at any non-saturating concentrations of lidocaine, a larger fraction of the myometrial sodium channels would be blocked than the myocardial sodium channels. Secondly, the ED$^{50}$ for blocking the sodium channel is 0.1 mM for the pregnant rat uterine myocyte (FIG. 4) contrasted to 0.5 mM for the rat cardiac ventricular myocyte[23]. Thus, the myometrial sodium channels are several times more susceptible to blockade by lidocaine than those in the myocardium. The combination of these two factors suggests that a serum concentration of lidocaine could be achieved and maintained which would block myometrial sodium channels effectively to influence uterine excitability, without blocking enough myocardial sodium channels to cause any substantive side-effects. Lacking information on the affinity of rat fetal or neonatal cardiac myocytes for lidocaine, a similar assessment cannot be made. However, from impalement microelectrode studies of cardiac Purkinje fibers from adult and neonatal dogs, the concentration of lidocaine necessary to produce the same degree of interference with the sodium channel was 2 to 2.5 times higher in the neonatal than the adult tissue[24].

In freshly dissociated myocytes from the term human uterus, voltage-gated sodium channels similar to those studied more extensively in rat uterine myocytes have also been found (unpublished observations of S. Y. Wang, C. Y. Kao and D. Nanda). Therefore, the present observations on the rat uterine myocyte and the above risk assessment bear direct relevance to the usefulness of lidocaine in the management of preterm labor in humans.

Advantages of the use of lidocaine in the management of preterm labor are: (a) the wealth of extant knowledge and clinical experience based on its use in cardiac antiarrhythmic therapy; (b) the absence of serious side-effects on either the mother or the fetus, in dosages used in continuous epidural anesthesia for labor[25], in which the maternal serum concentration attained (2.5 µg/ml) is comparable with the therapeutic level for antiarrhythmic action[19]; (c) its immediate availability; and (d) its low cost.

Other class 1 cardiac antiarrhythmic agents which affect the voltage-gated sodium channel may also be useful to manage preterm labor and the other indications discussed above. Some of these agents have the advantage of being effective by oral administration, and might be suitable for maintenance therapy over weeks, a time-frame long enough to make some meaningful differences in the pregnancy outcome.

Salts encompassed within the term "pharmaceutically acceptable salts" refer to non-toxic salts of the Class I cardiac antiarrhythmic compounds useful in this invention.

Conventional non-toxic salts include those derived from nonorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. For lidocaine, the hydrochloride salt is preferred.

The pharmaceutically acceptable salts of the Class I cardiac antiarrhythmic compounds can be synthesized from the compounds which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of the Class I cardiac anti-arrhythmic compounds are also readily prepared by conventional procedures such as treating such an acid with an appropriate amount of a base, such as an alkali or alkaline earth metal hydroxide, e.g., sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

Representative salts include the following salts:

| | |
|---|---|
| Acetate | Lactate |
| Benzenesulfonate | Lactobionate |
| Benzoate | Laurate |
| Bicarbonate | Malate |
| Bisulfate | Maleate |
| Bitartrate | Mandelate |
| Borate | Mesylate |
| Bromide | Methylbromide |
| Calcium Edetate | Methylnitrate |
| Camsylate | Methylsulfate |
| Carbonate | Mucate |
| Chloride | Napsylate |
| Clavulanate | Nitrate |
| Citrate | N-methylglucamine |
| Dihydrochloride | Oxalate |
| Edetate | Pamoate (Embonate) |
| Edisylate | Palmitate |
| Estolate | Pantothenate |
| Esylate | Phosphate/diphosphate |
| Fumarate | Polygalacturonate |
| Gluceptate | Salicylate |
| Gluconate | Stearate |
| Glutamate | Subacetate |
| Glycollylarsanilate | Succinate |
| Hexylresorcinate | Tannate |
| Hydrabamine | Tartrate |
| Hydrobromide | Teoclate |
| Hydrochloride | Tosylate |
| Hydroxynapthhoate | Triethiodide |
| Iodide | Valerate |
| Isethionate | |

The term "pharmacologically effective amount" shall mean that amount of a drug or pharmaceutical agent that will elicit the biological or medical response of a tissue, system, animal or human that is being sought by a researcher or clinician.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "cesarean delivery" shall mean incision through the abdominal and uterine walls for delivery of a fetus.

The term "Class I cardiac antiarrhythmic" refers to the antiarrhythmic drugs classified as Class I according to the pattern of electrophysiological effects that they produce and/or their presumed mechanisms of action as set forth in standard pharmacological texts, such as those in Table 3 of *Drug Evaluations*, 6th edition, American Medical Association and W. B. Saunders Company, 1986, p. 438. For example, Class 1A compounds include quinidine, procainamide, disopyramide; Class 1B compounds include lidocaine, phenytoin, tocainide and mexiletine; and Class 1C compounds include encainide, flecainide, lorcainide and propafenone. Class 1B compounds are the preferred compounds for use in the invention. Lidocaine is the most preferred compound.

In the present invention, it has been discovered that lidocaine can reduce the frequency and force of contractile activity in uterine smooth muscle, therefore, it may arrest premature labor or threatened abortion. Therefore, it is useful where needed for relaxing uterine smooth muscle or for inhibiting or reducing uterine contractile activity, and is adaptable to being used in a composition for treating premature labor.

The process of the present invention of inhibiting sodium channel induced contractions such as the uterine contractions of premature labor may be carried out by administering a therapeutic dose of lidocaine or other Class 1 cardiac antiarrhythmic compound.

The appropriate Class I cardiac antiarrhythmic compounds may be administered to a human subject either alone or, preferably, in combination with pharmaceutically-acceptable carriers or diluents, in a pharmaceutical composition, according to standard pharmaceutical practice. The compounds can be administered orally or parenterally, including intravenous, intramuscular, intraperitoneal, subcutaneous, and topical administration.

For oral use of the Class I cardiac antiarrhythmic compounds or pharmaceutically acceptable salts thereof according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a Class I cardiac antiarrhythmic compound is used to block sodium channels in uterine myocytes in a human subject to manage preterm labor, the daily dosage will normally be determined by the prescribing physician with the dosage generally varying according to the age, weight, and response of the individual patient, as well as the severity of the patient's symptoms. In general, the daily dosage will be within or below (e.g. one-half to one-third) the range shown to be safe and effective for use in the management of cardiac arrythmia, and the dosage may be in single or divided doses. For example, in most instances, an effective daily dosage of lidocaine will be one that will produce a serum concentration in the range from less than to about 1.5 ug/ml to 5 ug/ml when administered intravenously and an effective daily dosage of tocainide will be in the range of from less than to about 400 mg to about 800 mg per dose administered orally in three doses. In some cases, however, it may be necessary to use dosages outside these limits.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

Effects of Lidocaine on Ionic Currents of Uterine Myocytes

MATERIALS AND METHODS

All experiments in this study were performed under institutional guidelines for the care and use of laboratory animals (approval #92–055). Rats (Sprague-Dawley) were mated individually in the inventors' laboratory, and the duration of gestation was timed from the morning of the first discovery of cervical plugs. At the time of the acute experiment, the duration of gestation was confirmed by comparing the fetal sizes with known standards[14]. Individual myocytes were freshly isolated from 14 to 21-day pregnant uteri. Details of the methods of isolating the myocytes in a near-physiological condition, and associated patch-clamping can be found in other publications[7,15]. Briefly, strips of isolated longitudinal myometrium were incubated in collagenase, and then subjected to mild mechanical disruption, until individual myocytes in desired amounts were obtained. For the work described herein, such single freshly dissociated myocytes were studied in the whole-cell configuration of patch-clamping[9].

The bath solution in which the individual myocytes were studied contained (in mM): NaCl, 135; KCl, 5.4; $MgCl_2$, 1; $CaCl_2$, 3; HEPES, 10; and glucose 5. Lidocaine (Astra Pharmaceutical, Worcester, Mass. 01606), when used, was dissolved into the bath medium. The pipette solution contained (in mM): CsCl, 120; EGTA, 1; $Na_2ATP$, 2; HEPES, 10; K-pyruvate, 5; K-oxaloacetate, 5; and K-succinate, 5. All solutions were adjusted to pH 7.3; all experiments were done at room temperature of ca. 22° C. In the whole-cell mode of recording, rupture of the cell membrane allows access of the pipette solution to the cell interior. The reason for using CsCl rather than KCl is that the $Cs^+$ effectively blocks outward $K^+$ currents, and allows the inward currents to be isolated for study. For isolating the outward current, tetrodotoxin (Hebei preparation, from Calbiochem, San Diego, Calif. 92112) and nisoldipine (Miles Laboratory, New Haven, Conn. 06509) were used to block the inward currents. In the inventors' experience, the inclusion of the Krebs cycle substrates in the pipette solution minimized a time-related decline ("rundown") of the $Ca^{2+}$-currents. The basic properties of the voltage-gated sodium and calcium channels are described in detail in Yoshino et al[7].

RESULTS

Effects of lidocaine on ionic currents of uterine myocytes

As in many other excitable cells containing voltage-gated ionic channels in their surface membranes, uterine myocytes produce inward and outward currents upon appropriate depolarization. Depolarization converts closed ionic channels in the resting state to an open and conducting state, through which ionic fluxes produce currents. In mammalian smooth myocytes (e.g., intestinal myocytes[15], uterine myocytes[7]), there is much temporal overlap between the inward and outward currents, frustrating efforts to understand each current properly. For clarity, inward and outward currents are isolated by using appropriate specific blocking agents and the effects of lidocaine on the isolated inward and outward currents are discussed separately.

Inaction of lidocaine on outward currents

Figures 1A, 1B:
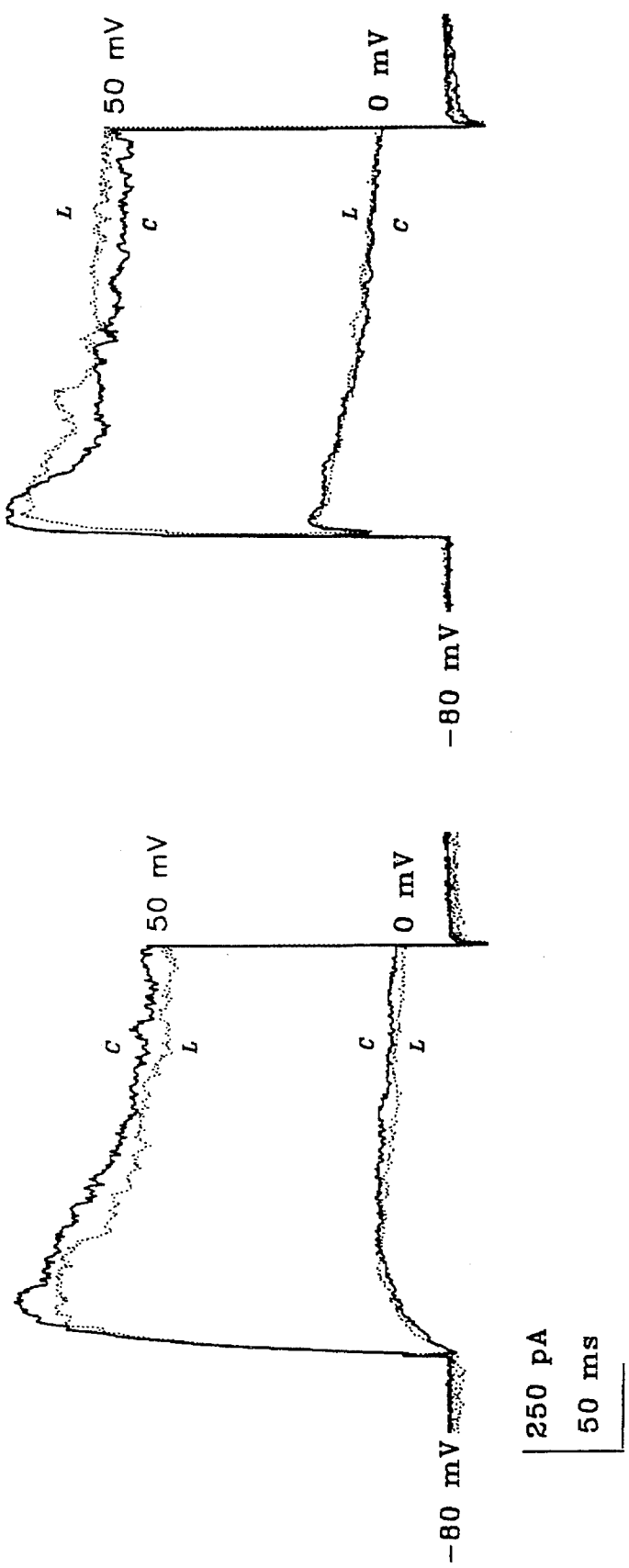
FIGS. 1A and B. Inaction of lidocaine on outward potassium currents of freshly dissociated myocytes from late-pregnant rat uterus. (A) Myocyte from 19-day pregnant uterus. Total cell capacitance (a reflection of cell size), 41 pF. (B) Myocyte from 19-day pregnant rat uterus, 49 pF. The myocytes selected were relatively small as compared with those used for inward current studies, in order to accentuate any possible effects of lidocaine. The concentration of lidocaine (0.5 mM) was the highest used (see later Figures). The cells were held at −80 mV, and then subjected to 250 ms depolarizing steps in 10 mV increments from −70 to 70 mV. Inward currents had been blocked with 1 μM tetrodotoxin and 2 μM nisoldipine in the bath. For clarity, only selected current traces for each myocyte are shown, with the command voltages attached to each. The solid traces are currents in the absence of lidocaine. Superimposed are currents recorded after 5 min in 0.5 mM lidocaine (broken lines). The effects of lidocaine are rather minor, and cannot be definitively distinguished from some progressive deterioration of the myocyte.

The outward currents of uterine myocytes have been isolated for study by adding to the bathing medium 1 μM of tetrodotoxin to block $Na^+$ currents and 2μM of nisoldipine to block $Ca^{2+}$ currents (FIG. 1). The outward currents are complex and contain contributions from several different classes of $K^+$ channels[8]. Moreover, the relative contributions from different classes change during the course of pregnancy[8]. Germane to the present study is the observation that lidocaine, even up to 0.5 mM, has insignificant effects on the overall K$^+$ current of the single uterine myocyte from late-pregnant uteri (FIG. 1).

Effects of lidocaine on inward currents

Figure 2C:
FIG. 2A, B, C, D, E and F. Effects of lidocaine on the inward sodium and calcium currents of a freshly dissociated rat uterine myocyte. Myocyte from 14-day pregnant rat uterus; 96 pF. Holding potential, −80 mV; depolarized by 35 ms steps from −40 mV in 10 mV increments to 30 mV. Meticulous capacitance cancellation was applied, as evidenced by the small residual artifact. Traces shown represent inward currents in response to applied voltage commands, outward $K^+$ currents having been blocked by the use of $Cs^+$-filled electrode. Inward currents consist of a fast component ($I_{Na}$) and a slower and more sustained component ($I_{Ca}$). At the end of the step voltage-commands, tail currents reflect $I_{Ca}$, because $I_{Na}$ is fully inactivated by this time. (A) Control, pre-lidocaine state. Symbols below the current traces indicate where current values are taken for I—V plots in panels E and F. (B) 1 mM lidocaine for 3 min. Note that $I_{Na}$ is completely blocked, whereas $I_{Ca}$ is 93% of that in (A). (C) Recovery from lidocaine, 6 min. $I_{Na}$ is 83% and tail $I_{Ca}$ is 86% of those in (A), suggesting either incomplete recovery from lidocaine or some progressive deterioration of the myocyte. (D) 0.5 mM lidocaine for 3 min. $I_{Na}$ is reduced to 25% and tail $I_{Ca}$ to 78% of those in (C). (E) Current-voltage (I—V) relations of $I_{Na}$ in panels (A—D). Symbols correspond to those under current traces. (F) I—V relations of $I_{Ca}$. These I—V plots also clearly demonstrate the rather selective action of lidocaine on $I_{Na}$ of uterine myocytes.
Figure 2D:
Figure 2F:
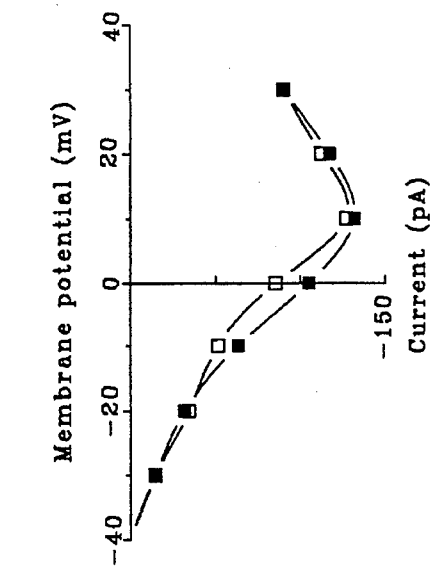
Figure 2A:
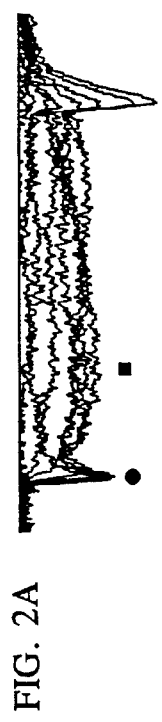
Figure 2B:
Figure 2E:
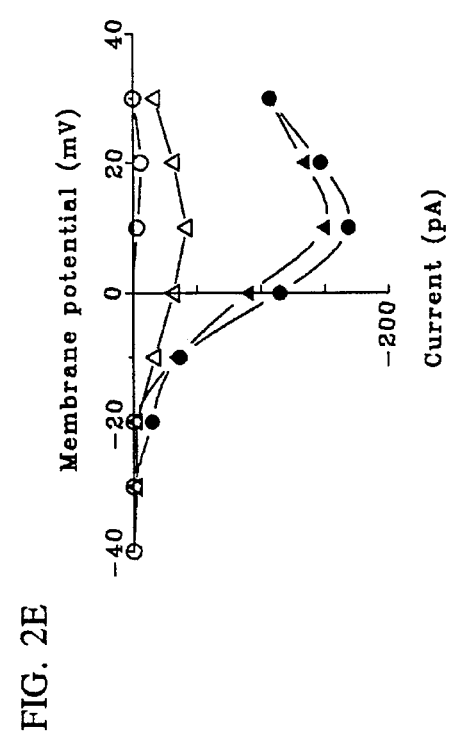

The inward currents have been isolated by using a pipette solution containing 120 mM Cs$^+$. FIGS. 2A and C show that on depolarization, the inward current in the uterine myocyte consists of two components; a fast component, characterized by rapid activation and rapid inactivation, which merges into a slower component, characterized by a slower activation and a much slower inactivation. On repolarization, an appreciable tail current is present. From detailed evidence given elsewhere[7], the fast current has been identified as a voltage-gated Na$^+$ current ($I_{Na}$), and the slower current and the tail-current have been identified as a voltage-gated Ca$^{2+}$ current ($I_{Ca}$). Briefly, the Na$^+$ current disappears in Na$^+$-free bathing media, and is fully blocked by 1 μM tetrodotoxin. The Ca$^{2+}$ current varies in magnitude according to the concentration of Ca$^{2+}$ in the bathing medium, and is blocked by nisoldipine (2 μM).

FIGS. 2 and 3 illustrates the typical responses of individual uterine myocytes to lidocaine applied in the bath solution. FIG. 2 also shows the reversible nature of the lidocaine effect. The myocyte was bathed in a medium containing 135 mM Na$^+$ and 3 mM Ca$^{2+}$, and $I_{Na}$ and $I_{Ca}$ were recorded for baseline reference (FIG. 2A). Then the bathing medium was changed to one containing 1 mM lidocaine. In 3 min, $I_{Na}$ completely disappeared, while $I_{Ca}$ and the tail-current were only slightly reduced (FIG. 2B). The medium was then changed back to the lidocaine-free solution, and in 6 min, $I_{Na}$ reappeared (FIG. 2C). Compared with the initial state, both $I_{Na}$ and $I_{Ca}$ were slightly smaller, possibly because of some residual effects of lidocaine, or of some deterioration of the myocyte. Nevertheless, when the myocyte was exposed to 0.5 mM lidocaine, most but not all of the $I_{Na}$ disappeared, and the Ca$^{2+}$ currents were again reduced slightly (FIG. 2D). The current-voltage relations under the different conditions are shown in FIGS. 2E and 2F.

FIG. 3 shows the effects of lidocaine on three other late-pregnant myocytes. For clarity, a lidocaine-affected trace is superimposed on a pre-lidocaine control trace of the same cell under identical voltage-clamp conditions. The recordings shown demonstrate the variable appearance of the complex inward currents where the $I_{Na}$ and $I_{Ca}$ can be distinctly separated or nearly merged. In each case, lidocaine affected primarily the $I_{Na}$. At 0.02 mM, the effect was so little that it appeared only as a slightly faster inactivation of the $I_{Na}$, and no detectable difference in $I_{Ca}$ (FIG. 3A). At 0.1 mM and 0.2 mM, the effects on $I_{Na}$ were unequivocal, and the effects on $I_{Ca}$ appeared only as slight reductions of the tail currents (FIG. 3B, C).

These current recordings and I–V relations illustrate not only the susceptibility of the myometrial Na$^+$ channel to lidocaine, but also the existence of significant differences in the sensitivity of the Na$^+$ and Ca$^{2+}$ channels to lidocaine.

Dose-response relations

FIG. 4 summarizes the responses of 21 myocytes from 17 different animals, exposed to various concentrations of lidocaine. The ordinate represents the residual fraction of current in lidocaine (I'$_{Na}$ or I'$_{Ca}$) normalized to the control baseline value before the application of lidocaine ($I_{Na}$ or $I_{Ca}$). For each concentration of lidocaine, the mean response of 4–5 myocytes are shown. For the effects on $I_{Na}$, the data are well fitted by a bimolecular reaction scheme (solid line), in which one molecule of lidocaine is presumed to have blocked one Na$^+$ channel (FIG. 4A). On $I_{Ca}$, the concentrations of lidocaine used, up to 0.5 mM, produced very little effect.

The dose-response relation on $I_{Na}$ can also be expressed in a Hill plot in which the log-log scale linearized the relation (FIG. 4B). The ordinate is log (1-P)/P, where P is I'$_{Na}$/I$_{Na}$. Least-squares linear regression fitting yields a curve with a slope of 1.2, which is consistent with a reaction without co-operativity. The concentration of lidocaine capable of blocking one-half of the Na$^+$ current (ED$_{50}$; when (1-P)/P= 1) is 0.11 mM. In contrast, the possible ED$_{50}$ for blocking the Ca$^{2+}$ current, extrapolated by assuming a similar bimolecular reaction, would be in excess of 10 mM (broken line, FIG. 4A). Thus, there is a marked difference (possibly several hundred fold) in the susceptibility of the Na$^+$ and Ca$^{2+}$ channels in uterine myocytes to blockade by lidocaine.

Effect of lidocaine on the "availability" of Na$^+$ channels

In general, voltage-gated ionic channels can exist in three states: closed, open, and inactivated, obligatorily influenced by the membrane voltage. For most channels, the closed state predominates in the resting state. Depolarization activates the channel into an open and conducting state. In an inactivated state, the channel cannot be opened by depolarization. Hence, the openability of a channel can be thought of as its "availability". In most excitable cells, a fraction of the total channel population exists in an inactivated state even at the usual resting potential, while the remainder are in the resting and closed state, "available" to open upon appropriate depolarization. Hyperpolarization removes inactivation, whereas depolarization enhances it. FIG. 5 shows the relation between membrane voltage and steady state inactivation of the Na$^+$ channel in uterine myocytes, in the presence and absence of lidocaine.

These studies were carried out with the usual two-pulse technique, in which a conditioning voltage-step was imposed on the myocyte to set the membrane voltage, and a test voltage-step was used to activate opening of the Na$^+$ channels. Such a protocol was applied to a single uterine myocyte in the control state, and was then repeated after 0.22 mM lidocaine (twice the ED$_{50}$) was applied to the same myocyte for 5 min. To avoid complications from coexisting $I_{Ca}$, 5 μM of nisoldipine was incorporated in the bathing medium to completely block the Ca$^{2+}$ channels. The data for the control state before lidocaine application were derived from 8 myocytes, but, because of technical difficulties of completing the entire experiment, data for the lidocaine-treated state were derived from 5 myocytes, all of which also provided data for the control state.

The steady-state inactivation relation for the control state is similar to that described in Yoshino et al.[7], but to the inventors' knowledge, that for lidocaine has not been demonstrated previously for the freshly dissociated uterine myocyte. The data are well fitted by Boltzmann distributions[16,17], where the voltage at which half of the Na$^+$ channels are inactivated is −64 mV in the control state and −74 mV in lidocaine. The slopes of the curves, which indicate the voltage-sensitivity of the inactivation process, are essentially similar in the two conditions. The negative shift of the "availability" curve caused by lidocaine has long been known to occur in various types of cardiac cells, and is considered to be the pharmacological basis of its antiarrhythmic actions[18,19]. Inspection of FIG. 5 shows that lidocaine similarly reduced the excitability of the uterine myocyte. Thus, at any membrane potential, the fraction of $Na^+$ channels "available" to be activated by depolarization in the lidocaine-affected state is less than that in the control state. For instance, at a membrane potential of −60 mV when about 35% of the $Na^+$ channel population are openable under physiological conditions, lidocaine would reduce that fraction to about 10%.

EXAMPLE 2

Effect of lidocaine on the duration of pregnancy

MATERIALS AND METHODS

In a separate set of experiments, pregnant rats were divided into two groups. Beginning on day-20 of gestation, one group (experimental) was given twice daily intramuscular injections of lidocaine in doses of 2, 4, and 6 mg/kg in 0.5 ml. of saline. The other group (control) was handled in the same way, except that the injections consisted of saline only. All these rats were allowed to go to term, and the dates of delivery were compared to see whether lidocaine had any effect in delaying parturition.

RESULTS

To test whether the excitability-reducing action of lidocaine on single uterine myocyte has any effect on the organ level, lidocaine (2, 4, or 6 mg/kg body weight) was given i. m. twice daily at 8 a.m. and 6 p.m., beginning on day-20 of gestation and continued until parturition. Logistic problems made a 12 a.m. dose impractical. Because the duration of pregnancy in the 4 control animals, which were given saline under the same protocol, were entirely similar to that of 5 additional rats used for other studies (but did not receive the sham saline injections), the data from these 9 animals were combined. Term in these 9 rats was 22.33±0.16 days (means ±S. E. M.). In the 8 rats treated with lidocaine, term was 23.63±0.39 days. If the two rats which received 2 mg lidocaine/kg and both of which delivered on the 23rd day were excluded on the ground that the dose of lidocaine was insufficient, then the remaining experimental group consisted of 6 rats, 2 receiving lidocaine at 4 mg/kg and 4 receiving lidocaine at 6 mg/kg. In this smaller experimental group, term was 23.83±0.40 days. Group comparison by Student's t-test shows that the difference between the means of the control and of either experimental group has p values of <0.01.

In all lidocaine-treated rats, the fetuses at birth or the newborn several hours after birth showed no discernable differences in motor activities from those born of untreated mothers. In one rat treated with 6 mg lidocaine/kg, pregnancy continued into the 26th day, a very long delay. To avoid possible post-term complications, it was sacrificed. At autopsy, the fetuses, on inspection, were healthy and indistinguishable from those of control newborns, except for their larger sizes.

The significant difference of 1.5 days in a 22-day gestation represents a 7% lengthening of the term.

EXAMPLE 3

Use of Lidocaine to Treat Pregnant Patients Who Present With Preterm Labor

MATERIALS AND METHODS

The gestational age of the fetus is preferably from 26 weeks to 34 weeks. There should be an absence of maternal or fetal conditions that will contraindicate stopping labor, such as bleeding or a congenital anomaly rendering the fetus incapable of survival. Preferably, uterine contractions should be at least 8 per hour or 4 in 20 minutes and cervical changes indicative of labor (e.g., effacement and dilatation) should be present. Membranes should not be ruptured. Preferably, there should be also be an absence of clinical infection, such as pyelonephritis; an absence of history of hypersensitivity to local anesthetics; and an absence of other contraindications to the use of lidocaine (e.g., Stokes Adams syndrome, Wolffe Parkinson White (WPW) syndrome, AV block or patients on pacemaker).

Procedure

A preliminary examination is done to record contraction frequency and Bishop's score (e.g., consistency, position of cervix, effacement and dilatation). A 12 lead base line ECG is taken and the patient placed on a fetal monitor, which will record fetal heart and uterine contractions. A maternal cardiac monitor is also attached. Lidocaine is administered intravenously at an initial loading dose of 75 mg, followed by rapid infusion at 8 mg/min to attain a serum concentration of 1.5–5 ug/ml (generally accepted as safe therapeutic range in management of cardiac arrhythmic). Serum concentrations are determined in the clinical laboratory, and results reported as rapidly as possible. After 20 min of infusion at 8 mg/min, infusion is to be slowed to 1–5 mg/min depending on clinical progress, both in terms of uterine contractions, and electro-cardiographic monitoring for possible side-effects. The therapy will continue for 12 additional hours after all contractions have ceased. After short-term effectiveness has been demonstrated further studies will be undertaken with respect to maintenance therapy. Treatment will be discontinued when either (a) the patient continues to progress in labor as demonstrated by continuing contractions and/or change in Bishop score of more than three over the previous score or (b) adverse reactions to therapy develop.

If the in-hospital treatment with intravenous infusion of lidocaine is effective in arresting premature uterine contractions, and no premature contractions recur within 48 hours, the patient could be discharged. At home, she could be maintained on tocainide by mouth in three doses of 200–400 mg per dose daily until term, with daily telephone reporting of status and/or side-effects.

RESULTS

It is expected that lidocaine will arrest or reduce premature labor contractions in the pregnant patients.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth hereinabove may be applicable as a consequence of variations in the responsiveness of the pregnant woman being treated for prevention of preterm labor, or for the other indications indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

INDUSTRIAL APPLICABILITY

The ability of the Class I cardiac antiarrythmics, such as lidocaine, to inhibit voltage gated sodium channels makes these compounds useful as pharmaceutical agents for mammals, especially for humans, for the treatment and prevention of disorders including preterm labor. These compounds may also find usefulness for stoppage of labor preparatory to Caesarian delivery.

REFERENCES

1. Rush R W, Keirst M J W, Howat P, Baum J D, Anderson A B M, Turnbull A C. Contribution of preterm delivery to perinatal mortality. Brit Med J 1976;2:965–968.
2. Committee to Study the Prevention of Low Birth Weight. Preventing low birth weight. Washington: National Academy Press 1985.
3. Creasy R J, Merkatz I R. Prevention of preterm birth: clinical opinion. Obstet Gynecol 1990;76:2S-6S.
4. Morrison J C. Preterm birth: A puzzle worth solving. Obstet Gynecol 1990;76:5S–12S.
5. Canadian Preterm Labor Investigators Group. Treatment of preterm labor with the beta-adrenergic agonist ritodrine. New England J Med 1992;327:308–312.
6. Norton M G, Merrill J, Cooper B A B, Kuller J A, Clyman R I. Neonatal complications after the administration of indomethacin for preterm labor. New England J Med 1993;329:1602–1607.
7. Yoshino M, Wang S Y, Kao C Y. Sodium and calcium inward currents in freshly dissociated smooth myocytes of pregnant rat uterus. J Gen Physiol 1993 (under review).
8. Yoshino M, Wang S Y, Sui J L, Wakui M, Kao C Y. Potassium currents of the freshly dissociated smooth myocytes of pregnant rat uterus. J Gen Physiol 1993 (under review).
9. Hamill O P, Marty A, Neher E, Sakmann B, Sigworth F J. Improved patch clamp technique for high-resistance current recording from cells and cell-free membrane patches. Pflugers Arch 1981;391:85–100.
10. Yoshino M, Wang S Y, Kao C Y. Ionic currents in smooth myocytes of the pregnant rat uterus. J Gen Physiol 1991;94:38a.
11. Ohya Y, Sperelakis N. Fast $Na^+$ and slow $Ca^{2+}$ channels in single uterine muscle cells from pregnant rats. Am J Physiol 1989;257:C408–412.
12. Young R C, Hernon-Smith L. Characterization of sodium channels in cultured human uterine smooth muscle cells. Am J Obstet Gynecol 1991;164:175–181.
13. Nakai Y, Kao C Y. Changing proportions of $Na^+$ and $Ca^{2+}$ components of the early inward current in rat myometrium during pregnancy. Fed Proc 1983;42:313.
14. Witschi E. Development of Vertebrates. Philadelphia: Saunders, 1956:398.
15. Yamamoto Y, Hu S L, Kao C Y. Inward current in single smooth muscle cells of the guinea pig taenia coli. J Gen Physiol 1989;93:521–550.
16. Hodgkin A L, Huxley A F. The dual effect of membrane potential on sodium conductance in the giant axon of Loligo. J Physiol (Brit) 1952;116:497–506.
17. Hille B. Ionic Channels of Excitable Membrane. 2nd ed. Sunderland, M A: Sinauer 1991:42–43
18. Weidmann S. Effects of calcium ion and local anesthetics on electrical properties of Purkinje fibers. J Physiol (Brit) 1955;129:568–582.
19. Bigger J T Jr, Hoffman B F. Antiarrhythmic Drugs. In: Gilman A G, Rall T W, Nies A S, Taylor P, eds. Pharmacological Basis of Therapeutics. New York: Pergamon 1990:848–860.
20. Fan S F, Wang S Y, Kao C Y. The transduction system in the isoproterenol activation of the $Ca^{2+}$-activated $K^+$ channel in guinea pig taenia coli myocyte. J Gen Physiol 1993;102:257–275.
21. Casper R F, Lye S J. β-adrenergic receptor agonist infusion increases plasma prostaglandin F levels in pregnant sheep. Am J Obstet Gynecol 1987;157:998–1003.
22. Kunze D L, Brown A M. Cardiac sodium channels. In: Piper H M, Isenberg G, eds. Isolated Adult Cardiomyocytes. Vol II. Boca Raton, Fl. CRC Press 1989:15–28.
23. Malkielski J C, Fan Z. Phasic block of cardiac and nerve Na channels under uniform conditions. Biophys J 1993;64:A89
24. Mary-Rabine L, Rosen M R. Lidocaine effects on action potentials of Purkinje fibers from neonatal and adult dogs. J Pharmacol Exp Therap 1978;205:204–211.
25. Abboud T K, Frasiabi A, Sarkis F, Daftarian F, Nagappala S, Noueihed F, Kuhnert B R, Miller F. Continuous infusion epidural analgesia in parturients receiving bupivacaine, chloroprocaine, or lidocaine—maternal, fetal and neonatal effects. Anesth Analg 1984;63:421–428.

Every reference cited hereinbefore is hereby incorporated by reference in its entirety.

Modifications of the above described modes for carrying out the invention that are obvious to those of skill in the fields of chemistry, medicine, and related fields are intended to be within the scope of the following claims.

What is claimed is:

1. A method for inhibiting premature labor comprising administering to a subject having preterm labor contractions a composition comprising a therapeutic amount of a Class I cardiac antiarrhythmic compound in a pharmaceutically acceptable carder using a daily dosage within or below the range shown to be safe and effective for use in the management of cardiac arrhythmia to obtain serum levels sufficient to inhibit premature labor.

2. A method according to claim 1 wherein the compound is lidocaine.

3. A method according to claim 2 wherein the daily dosage is one that will produce a serum concentration in the range from about 1.5 ug/ml to about 5 ug/ml.

4. A method according to claim 1 wherein the compound is tocainide.

5. A method according to claim 4 wherein the daily dosage is three doses daily of about 200 mg to about 400 mg per dose.

6. A method according to claim 1 wherein the Class I cardiac antiarrythmic compound is a Class 1B cardiac antiarrythmic compound.

* * * * *